United States Patent [19]

Hawkins

[11] 4,046,749

[45] Sept. 6, 1977

[54] PHENYLENE SULFIDE OLIGOMER PRODUCTION

[75] Inventor: Richard T. Hawkins, Orem, Utah

[73] Assignee: Phillips Petroleum Company, Bartlesville, Okla.

[21] Appl. No.: 613,669

[22] Filed: Sept. 15, 1975

[51] Int. Cl.² .................. C08F 28/00; C08G 75/06
[52] U.S. Cl. .................................. 260/79; 260/79.1; 260/609 E
[58] Field of Search ................. 260/79, 79.1, 609 E

[56] References Cited

U.S. PATENT DOCUMENTS

| | | | |
|---|---|---|---|
| 3,524,835 | 8/1970 | Edmonds, Jr. et al. | 260/79.1 |
| 3,562,199 | 2/1971 | Hill, Jr. et al. | 260/37 |
| 3,647,752 | 3/1972 | Gieseking et al. | 260/609 E |
| 3,869,434 | 3/1975 | Campbell et al. | 260/79.1 |
| 3,948,865 | 4/1976 | Brady et al. | 260/79 |

*Primary Examiner*—Melvyn I. Marquis

[57] ABSTRACT

Phenylene sulfide oligomers are produced by heating at least one aromatic sulfide in an oxygen-containing gaseous atmosphere at an elevated temperature and for a period of time sufficient to form the oligomers. The oligomers can be cured by heating in an oxygen-containing atmosphere while the oligomers are being produced or in a subsequent step after production to yield cured oligomers having utility as coatings, films, and the like.

17 Claims, No Drawings

PHENYLENE SULFIDE OLIGOMER PRODUCTION

This invention relates to the production of phenylene sulfide oligomers. In accordance with another aspect, this invention relates to the production of phenylene sulfide oligomers by heating at least one aromatic sulfide in an oxygen-containing gaseous atmosphere. In accordance with another aspect, phenylene sulfide oligomers are produced by heating at least one aromatic sulfide in an oxygen-containing atmosphere and in the presence of a free radical generator. In accordance with another aspect, phenylene sulfide oligomers produced according to the invention are cured while being produced or subsequent to production by heating at an elevated temperature in an oxygen-containing atmosphere.

Accordingly, an object of this invention is to provide a process for the production of phenylene sulfide oligomers.

Another object of this invention is to provide a process for curing phenylene sulfide oligomers.

Another object of this invention is to provide a process for production of cured phenylene sulfide oligomers having utility as coatings, films, and the like.

Other objects, aspects, and the several advantages of the invention will be apparent to those skilled in the art upon reading the specification and the appended claims.

In accordance with this invention, phenylene sulfide oligomers are produced by heating at least one aromatic sulfide having the formula

where $m$ is an integer of 1, 2, or 3 and where the structure of each

is selected from

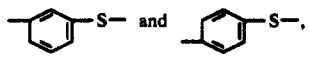

at a temperature and for a period of time sufficient to form the oligomers, in an atmosphere of an oxygen-containing gas.

Aromatic sulfides which can be employed as reactants in producing the phenylene sulfide oligomers include 1,3-bis(phenylthio)benzene, 1,4-bis(phenylthio)benzene, bis[m-(phenylthio)-phenyl] sulfide, bis[p-(phenylthio)phenyl] sulfide, m-(phenylthio)-phenyl p-(phenylthio)phenyl sulfide, 1,3-bis[m-(phenylthio)phenylthio]benzene, 1,4-bis[p-(phenylthio)phenylthio]benzene, 1-[m-(phenylthio)phenylthio]-4-[p-(phenylthio)phenylthio]benzene, and the like, and mixtures thereof.

Phenylene sulfide oligomers which can be produced by the process of this invention can be represented by the formula

where $n$ is an integer of 2 to about 12 and where the structure of each

is selected from

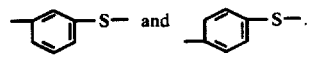

Although the temperature at which the reaction is conducted can vary over a considerable range, generally it will be within the range of about 270° C to about 420° C, preferably about 300° C to about 395° C. The temperature preferably is raised gradually as the reaction proceeds, particularly when the lower molecular weight aromatic sulfide reactants are employed, thereby avoiding substantial volatilization of the sulfide reactant. The reaction time can vary considerably, depending in part on the reaction temperature, but generally will be within the range of about 1/4 hour to about 24 hours, preferably about 3 hours to about 8 hours.

The reaction is conducted in an atmosphere of an oxygen-containing gas such as air. Preferably the reaction is conducted while passing the oxygen-containing gas through the aromatic sulfide reactant, thereby aiding in removing by-products of lower molecular weight, e.g., diphenyl sulfide. The pressure is not critical but should be sufficient to avoid substantial volatilization of aromatic sulfide reactant, although it preferably is sufficiently low to permit volatilization of by-products of lower molecular weight, e.g., diphenyl sulfide, particularly during the latter part of the reaction.

Although the use of an added free radical generator is not required, preferably a free radical generator is admixed with the aromatic sulfide reactant, particularly when the reaction is conducted at the lower temperatures. Any free radical source capable of generating a substantial concentration of free radicals at the reaction temperature employed can be used. Examples of some free radical generators which can be employed include disulfides such as diphenyl disulfide and di-α-naphthyl disulfide, sulfur, and organic peroxides, including hydroperoxides, such as α,α-dimethylbenzyl hydroperoxide, 1-phenylcyclohexyl hydroperoxide, tert-butyl hydroperoxide, di-α,α-dimethylbenzyl peroxide, di-tert-amyl peroxide, and the like. Although the amount of free radical generator is not critical, generally, if used, it will be employed in an amount up to about 5 weight percent, preferably in an amount of about 0.5 weight percent to about 3 weight percent, based on the total weight of aromatic sulfide reactant plus free radical generator.

If desired, lower boiling by-products such as diphenyl sulfide can be separated from the reaction mixture during or after the reaction period by volatilization of these by-products. Some aromatic sulfide reactants also can be at least partially volatilzed from the reaction mixture during or after the reaction period. If desired, the more soluble phenylene sulfide oligomers, i.e., those of lower molecular weight and those having

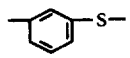

units, can be separated from other phenylene sulfide oligomer products by extraction with solvents such as benzene, toluene, xylenes, dimethyl sulfoxide, N-methyl-2-pyrrolidone, or the like.

The phenylene sulfide oligomers produced by the process of this invention can be blended with fillers, pigments, extenders, other polymers, and the like. The oligomers can be cured through crosslinking and chain extension, e.g., by heating at temperatures of about 310° C to about 480° C, preferably about 380° C to about 430° C, for a period of time within the range of about 10 minutes to about 24 hours, preferably about 30 minutes to about 3 hours, and in the presence of a free oxygen-containing gas such as air, to provide cured products having high thermal stability and good chemical resistance. At the lower curing temperatures, e.g., about 310° C to about 350° C, the curing should be conducted in the presence of a cure promoter such as sulfur, 2,2'-azobis(2-methylpropionitrile), organic peroxides such as those applicable in the production of the oligomers, copper, etc. At temperatures higher than about 350° C, use of the cure promoter is optional. If desired, the cure promoter can be used in amounts as high as 25 weight percent, based on the total weight of phenylene sulfide oligomers plus cure promoter. The oligomers can be cured to provide useful molding resins, coatings, and adhesives. Although any of the oligomers can be employed with or without a diluent in the production of coatings and adhesives, the more soluble phenylene sulfide oligomers, i.e., those of lower molecular weight and those containing

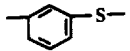

units, can be used as solutions in solvents such as benzene, toluene, xylenes, dimethyl sulfoxide, N-methyl-2-pyrrolidone, or the like.

At relatively high temperatures, e.g., at about 390° C to about 420° C, in an atmosphere of an oxygen-containing gas such as air, the curing of phenylene sulfide oligomers produced from aromatic sulfide reactants as defined above in which m is 2 or 3 can be conducted, e.g, within a period of about 30 minutes to about 3 hours, while the oligomers are being produced, in a single process step. As examples, cured coatings or films can be produced in this manner.

EXAMPLE I

In a 50-ml cone-shape, two-neck flask equipped with thermometer, capillary inlet dipping to the bottom of the flask, a simple distillation takeoff, and a receiver was placed 11.71 g 1,4-bis(phenylthio)benzene. The contents of the flask were heated for seven hours at a temperature of 308°-375° C, while bubbling air into the contents, with the intermittent application of partial vacuum during the last half of the heating period. During the heating period 3.00 g of distillate (Fraction 1) was collected. The residual mixture which did not distill was extracted by heating with 60 ml of refluxing benzene, cooling the resulting mixture to about 25° C, and filtering, thereby obtaining 3.00 g of tan powder (Fraction 2) melting at 178°-210° C. Evaporation of benzene from the filtrate yielded 5.62 g of soft, sticky, brown semisolid material (Fraction 3).

Analysis of Fractions 1, 2, and 3 indicated the composition of these fractions to be as shown in Table I.

TABLE I

| | | Weight, g, of $\langle\bigcirc\rangle-S+\langle\bigcirc\rangle-S\frac{}{n}\langle\bigcirc\rangle$ where n is | | | | |
|---|---|---|---|---|---|---|
| Fraction | Weight, g | 0 | 1 | 2 | >2[a] | >>2[b] |
| 1 | 3.00 | 2.86 | 0.14 | | | |
| 3 | 5.62 | 1.91 | 1.52 | 0.98 | 1.21 | |
| 2 | 3.00 | | | | | 3.00 |
| Total | 11.62 | 4.77 | 1.66 | 0.98 | 1.21 | 3.00 |

[a]Most of this material had a value for n of 3 or 4.
[b]This material had an average value for n of about 6.6.

The analysis of Fraction 1 was conducted by gas chromatography. Analysis for sulfur in Fraction 2 showed the sulfur content to be 27.07 weight percent, indicating this fraction to have an average molecular weight of 900 and an average value for n, as shown in Table I, of about 6.6. Gel permeation chromatography of a sample of Fraction 2 in 1,2,4-trichlorobenzene at 130° C showed the sample had a narrow molecular weight distribution, the heterogeneity index (ratio of weight average molecular weight to number average molecular weight) being 1.67. Gas chromatographic analysis of Fraction 2 indicated the absence of substances having a value for n, as shown in Table I, of less than 3. Fraction 3 was analyzed by gas chromatography, whereby the weight ratio of the three lowest members of the series of compounds having the formula shown in Table I, namely, of those compounds represented by the formula with n equal to 0, 1, and 2, was ascertained to be 43.2 to 34.4 to 22.2, respectively. Then a portion of Fraction 3 was subjected to short-path simple distillation using a maximum kettle temperature of 160° C at 3 mm Hg pressure, thereby providing a distillate comprising 94.3 weight percent and 5.7 weight percent of products represented by the formula in Table I where n is 0 and 1, respectively. Gas chromatographic analysis of the residue remaining after the distillation showed the presence of none of the substance represented by the above-mentioned formula with n equal to 0, whereas the ratio of the substance represented by this formula in which n is 1 to that in which n is 2 was essentially the same as that previously found in Fraction 3 prior to distillation. The remainder of the residue remaining after distillation comprised substances of the above formula in which n is greater than 2, principally 3 or 4. These data enabled calculation of the composition of Fraction 3, as shown in Table I. Infrared spectra of Fractions 1, 2, and 3, as well as of the distillate and residue obtained from Fraction 3, were consistent with those to be expected for substances having the indicated structures.

Thus, p-phenylene sulfide oligomers were produced by heating 1,4-bis(phenylthio)benzene under the conditions described.

A sample of Fraction 2 was cured to a film by heating in air for 2 hours at 390°-400° C on an aluminum substrate.

EXAMPLE II

Another oligomerization was conducted, this time on a larger scale and in the presence of a minor amount of diphenyl disulfide.

In a 50-ml cone-shape, two-neck flask equipped as described in Example I were placed 21.78 g 1,4-bis(phenylthio)-benzene and 0.50 g diphenyl disulfide. The mixture was heated for seven hours at a temperature of 309°–370° c, while bubbling air into the mixture, with the intermittent application of partial vacuum during the last two hours of the heating period. During the heating period 7.54 g of distillate (Fraction 1), principally diphenyl sulfide, was collected, any 1,4-bis(phenylthio)benzene present being insufficient to be readily discernible by infrared analysis. The residual mixture which did not distill was extracted by heating with 135 ml refluxing benzene, cooling the resulting mixture to about 25° C, and filtering, thereby obtaining as a tan powder 7.10 g of p-phenylene sulfide oligomers (Fraction 2) melting at 205°–225° C and exhibiting an infrared spectrum virtually identical to that of the benzene-insoluble oligomers obtained in Example I. Evaporation of benzene from the filtrate yielded 7.47 g of straw-colored, soft, sticky semisolid material (Fraction 3) comprising diphenyl sulfide, 1,4-bis(phenylthio)benzene, and lower p-phenylene sulfide oligomers found in Fraction 3 in Table I, based on its infrared spectrum.

Cured films were prepared by heating, in air, compositions comprising the p-phenylene sulfide oligomers melting at 205°–225° C on aluminum substrates, in the presence or absence of selected additives, as summarized in Table II.

TABLE II

| Additive | | Curing Conditions | | |
|---|---|---|---|---|
| Substance | Concentration, weight percent[a] | Time, hr. | Temperature, °C | Remarks |
| None | — | 2 | 400 | Tough, flexible film |
| Sulfur | 15.0 | 2 | 310–315 | Tough, glossy, transparent, brittle film |
| 2,2'-Azobis(2-methylpropionitrile) | 11.3 | 2 | 315 | Glossy, brittle film |
| α,α-Dimethylbenzyl hydroperoxide | 20.3 | 2 | 315 | Glossy, brittle film |
| Copper | 13.1 | 2 | 315 | Mostly flexible film; glossy, transparent film in part |

[a]Based on combined weight of oligomers and additives.

EXAMPLE III

In an oligomerization conducted by a procedure similar to that used in Example II, using the same equipment, a mixture of 22.03 g 1,4-bis(phenylthio)benzene and 0.53 g diphenyl disulsulfide was heated for seven hours at a temperature of 312°–395° C, while bubbling air into the mixture, with the brief application of partial vacuum after about five hours of heating. During the heating period 10.30 g of distillate (Fraction 1), principally diphenyl sulfide, was collected. The residual mixture which did not distill was extracted by heating with refluxing benzene, cooling the resulting mixture to about 25° C, and filtering, thereby obtaining as a tan powder 7.72 g of p-phenylene sulfide oligomers (Fraction 2) melting at 224°–244° C. Evaporation of benzene from the filtrate yielded 4.54 g of sticky semisolid material (Fraction 3) comprising diphenyl sulfide, 1,4-bis(phenylthio)benzene, and lower p-phenylene sulfide oligomers found in Fraction 3 in Table I. The infrared spectra of Fractions 1, 2, and 3 in this example were virtually the same as those of Fractions 1, 2, and 3, respectively, in Example II. Analysis for sulfur in a sample of the oligomers melting at 224°–244° C showed the sulfur content to be 27.33 weight percent, indicating this fraction to have an average molecular weight of 1,000. Thus, the composition of this fraction can be represented by the formula shown in Table I, with an average value for $n$ of about 7.6. A sample of this fraction was cured to a tough, flexible film by heating in air for two hours at 400°–420° C on an aluminum substrate.

EXAMPLE IV

In a 50-ml cone-shape, two-neck flask equipped as described in Example I was placed 3.29 g bis[p-(phenylthio)phenyl] sulfide. The contents of the flask were heated for seven hours at a temperature of 320°–378 C, while bubbling air into the contents. No vacuum was applied, and no distillate was collected. The reaction mixture was extracted by heating with 40 ml of refluxing benzene, cooling the resulting mixture to about 25° C, and filtering, thereby obtaining as a brown solid 1.27 g of a mixture of p-phenylene sulfide oligomers melting at 210°–228° C, the infrared spectrum of which was consistent with that to be expected for the mixture. Evaporation of benzene from the filtrate yielded 2.00 g of semisolid material comprising diphenyl sulfide, 1,4-bis(phenylthio)-benzene, and lower p-phenylene sulfide oligomers found in Fraction 3 in Table I.

EXAMPLE V

In a 50-ml cone-shape two-neck flask equipped as described in Example I were placed 23.81 g 1,3-bis(phenylthio)-benzene and 0.52 g diphenyl disulfide. The contents of the flask were heated for seven hours at a temperature of 313°–389° C, while bubbling air into the contents, with the intermittent application of partial vacuum during the last three hours of the heating period. During the heating period 8.12 g of clear, colorless distillate was collected. The infrared spectrum of this distillate indicated it to be mostly diphenyl sulfide, with a small amount of 1,3-bis(phenylthio)benzene and a trace of thiophenol present. The residual mixture, a thick, dark, benzenesoluble oil, which did not distill was extracted by heating with about 100 ml of refluxing ethanol, cooling the resulting mixture to about 25° C, and filtering, thereby obtaining as brown, soft, sticky, benzene-soluble granules 10.75 g of a mixture of m-phenylene sulfide oligomers. Analysis for sulfur in this mixture of oligomers showed the sulfur content to be 25.93 weight percent. Thus, the average molecular weight of this mixture of oligomers was 620, and this mixture of oligomers can be represented by the formula

where the average value for n is 4.0. The infrared spectrum of this mixture of oligomers was consistent with that to be expected for a mixture having the above composition. Evaporation of ethanol from the ethanolic extract obtained after the above filtration yielded 4.51 g of cloudy yellow oil comprising mostly diphenyl sulfide and 1,3-bis-(phenylthio)benzene, based on infrared analysis.

A portion of the above mixture of m-phenylene sulfide oligomers having an average molecular weight of 620 was cured to a tough, flexible film by heating in air for two hours at 400°–420° C on an aluminum substrate.

EXAMPLE VI

In a 50-ml cone-shape, two-neck flask equipped as described in Example I were placed 11.91 g 1,4-bis(phenylthio)benzene, 11.89 g 1,3-bis(phenylthio)benzene, and 0.52 g diphenyl disulfide. The contents were heated for seven hours at a temperature of 314°–382° C, while bubbling air into the mixture, with the intermittent application of partial vacuum during the last three hours of the heating period. During the heating period 10.17 g of clear colorless distillate (Fraction 1) was collected. The residual dark, viscous, benzene-soluble oil was heated with a mixture of ethanol and benzene, the mixture was cooled, and the solvent phase was decanted from the dark putty-like phase, which would not crystallize. The solvent was evaporated from the solvent phase to give 2.17 g of a yellow oil (Fraction 2). Removal of solvent from the dark putty-like phase by maintaining the putty-like material in a vacuum oven for several days and then heating at about 125° C at 3 mm Hg until bubbling subsided yeilded 11.98 g of a dark, viscous oil (Fraction 3).

The infrared spectrum of Fraction 1 indicated this fraction to be mostly diphenyl sulfide, with small amounts of 1,4-bis(phenylthio)benzene, 1,3-bis(phenylthio)benzene, and thiophenol present. The infrared spectrum of Fraction 2 indicated this fraction to be predominantly diphenyl sulfide, 1,4-bis(phenylthio)benzene, and 1,3-bis(phenylthio)benzene. The infrared spectrum of Fraction 3 was consistent with that to be expected for a mixture of phenylene sulfide oligomers having both meta and para linkages. That this fraction was not merely a mixture of p-phenylene sulfide oligomers and m-phenylene sulfide oligomers was confirmed by solubility determinations. Thus, 0.41 g of Fraction 3 was completely soluble in 10.0 ml benzene, either at about 25° C or when hot. In contrast, a mixture of 0.2049 g p-phenylene sulfide oligomers (from Fraction 2, Example II) and 0.2151 g m-phenylene sulfide oligomers (from the 10.75 g of brown, soft, sticky, benzene-soluble granules isolated in Example VI) was only partially soluble in 11.0 ml benzene, either at about 25° C or when hot.

A portion of Fraction 3 was cured to a tough, flexible film by heating in air for two hours at 400°–420° C on an aluminum substrate.

EXAMPLE VII

A 0.1015 g sample of bis[p-phenylthio)phenyl] sulfide was heated in air, on an aluminum substrate, for one hour at 400°–410° C to produce a thin, cured film weighing 0.0013 g. The infrared spectrum of this film of cured p-phenylene sulfide oligomers was virtually the same as that of the cured film in Table II produced through use of sulfur as an additive except that the film of this example exhibited greater absorption at 1240 cm$^{-1}$ than did the film of Table II.

Thus, in this example formation of oligomers and curing of resulting oligomers occurred in a single process step.

I claim:

1. A process for the production of phenylene sulfide oligomers which comprises heating at least one aromatic sulfide having the formula

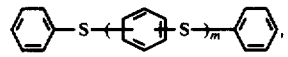

where m is an integer of 1, 2, or 3 and where the structure of each

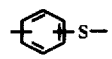

is selected from

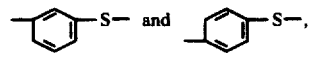

in an atmosphere of an oxygen-containing gas and at an elevated temperature and for a period of time sufficient to form a phenylene sulfide oligomer represented by the formula

where n is an integer of 2 to about 12 and where the structure of each

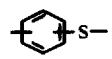

is selected from

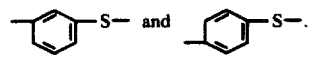

2. A process according to claim 1 wherein said heating is carried out in the presence of a free radical generator selected from sulfur, disulfides, and organic peroxides including hydroperoxides, capable of generating free radicals at the reaction temperature.

3. A process according to claim 1 wherein the phenylene sulfide oligomer obtained is subjected to additional heating in an atmosphere of an oxygen-containing gas at temperatures higher than about 350° C for a period of time sufficient to effect cure.

4. A process according to claim 1 wherein said oligomer is additionally heated to effect cure in an atmosphere of an oxygen-containing gas at a temperature in the range of about 310° C to about 480° C and in the presence of a cure promoter selected from sulfur, copper, 2,2'-azobis(2-methylpropionitrile) and organic peroxides including hydroperoxides.

5. A process according to claim 1 wherein $m$ is 2 or 3 and said heating is conducted at a temperature in the range of about 390° C to about 420° C for a period of time in the range of about 30 minutes to about 3 hours to effect phenylene sulfide oligomer production and curing in a single step.

6. A process according to claim 1 wherein said heating is carried out at a temperature in the range of about 270° C to about 420° C for a period of time ranging from about one-fourth hour to about 24 hours and under sufficient pressure to avoid substantial volatilization of aromatic sulfide reactant.

7. A process according to claim 1 wherein said aromatic sulfide is 1,4-bis(phenylthio)benzene and said oxygen-containing gas is air, and said heating is effected at a temperature in the range of about 300° C to about 395° C.

8. A process according to claim 1 wherein said aromatic sulfide is 1,4-bis(phenylthio)benzene and said oxygen-containing gas is air, said heating is effected at a temperature in the range of about 300° C to about 395° C, and said heating is carried out in the presence of diphenyl disulfide as a free radical generator.

9. A process according to claim 4 wherein said aromatic sulfide is 1,4-bis(phenylthio)benzene, said oxygen-containing gas is air, and said cure promoter is selected from sulfur, copper, 2,2'-azobis(2-methylpropionitrile) and α,α-dimethylbenzyl hydroperoxide.

10. A process according to claim 1 wherein said aromatic sulfide is a mixture of 1,4-bis(phenylthio)benzene and 1,3-bis-(phenylthio)benzene, said oxygen-containing gas is air, said heating is effected at a temperature in the range of about 300° C to about 395° C, and said heating is effected in the presence of diphenyl disulfide as a free radical generator.

11. A process according to claim 5 wherein said oligomer production and curing are effected in the presence of a cure promoter selected from sulfur, copper, 2,2'-azobis(2-methylpropionitrile), and organic peroxides including hydroperoxides.

12. A process according to claim 1 wherein said heating is initially effected at a lower temperature and increased as the reaction proceeds, thereby avoiding substantial volatilization of the sulfide reactant.

13. A process according to claim 1 wherein the oxygen-containing gas is passed through the aromatic sulfide reactant during heating, thereby aiding in removing by-products of lower molecular weight as the reaction proceeds.

14. A process according to claim 1 wherein said aromatic sulfide is bis[p-(phenylthio)phenyl] sulfide, said oxygen-containing gas is air, and said heating is effected at a temperature in the range of about 300° C to about 395° C.

15. A process according to claim 1 wherein said aromatic sulfide is 1,3-bis(phenylthio)benzene, said oxygen-containing gas is air, said heating is effected at a temperature in the range of about 300° C to about 395° C, and said heating is effected in the presence of diphenyl disulfide as a free radical generator.

16. A process according to claim 1 wherein the phenylene sulfide oligomer obtained is subjected to additional heating in the absence of a cure promoter at a temperature in the range of about 380° C to about 430° C for a period of time sufficient to effect cure.

17. A process according to claim 1 wherein the phenylene sulfide oligomer obtained is subjected to additional heating in an atmosphere of an oxygen-containing gas at a temperature in the range of about 310° C to about 350° C for a period of time sufficient to effect cure and in the presence of a cure promoter selected from sulfur, copper, 2,2'-azobis(2-methylpropionitrile) and organic peroxides including hydroperoxides.

* * * * *